United States Patent [19]  
Chang

[11] Patent Number: 4,854,303  
[45] Date of Patent: Aug. 8, 1989

[54] HAIR CIRCLE FOR CONJUGAL AFFECTION

[76] Inventor: Dao-Pin Chang, 55, Hou Hu, Hu Pei Tsun, Lin Kow Hsiang, Taipei Hsien, Taiwan

[21] Appl. No.: 111,436

[22] Filed: Oct. 21, 1987

[51] Int. Cl.⁴ .............................................. A61H 7/00
[52] U.S. Cl. ...................................... 128/62 R; 128/67
[58] Field of Search ................ 128/79, 67, 62 R; 15/191 R, 193

[56] References Cited

U.S. PATENT DOCUMENTS

| | | | |
|---|---|---|---|
| 2,024,983 | 12/1935 | Street | 128/79 |
| 2,559,059 | 7/1951 | Worstenholm | 128/79 |
| 3,633,572 | 1/1972 | Wiggins | 128/79 |
| 3,716,065 | 2/1973 | Finamore | 132/5 |
| 4,052,982 | 10/1977 | Ozeryansky | 128/60 |
| 4,224,933 | 9/1980 | Reiling | 128/79 |
| 4,488,541 | 12/1984 | Garcia | 128/79 |

FOREIGN PATENT DOCUMENTS 554178 7/1932 Fed. Rep. of Germany ........ 128/79  
443667 4/1975 U.S.S.R. .................................. 128/79

Primary Examiner—Gene Mancene  
Assistant Examiner—Cary E. Stone  
Attorney, Agent, or Firm—Lowe, Price, LeBlanc, Becker & Shur

[57] ABSTRACT

Hair circle for conjugal affection is described. The circle consists of a base member of elastic material having a plurality of mutually spaced round holes extending radially therethrough. A tuft of soft hair extends through each hole with a single tuft extending through a pair of holes. The hair tufts are secured by a adherent film coated on the inner surface of the base member. The tufts may be arranged in rows longitudinally, transverse, or in triangular shapes and the base member can have a cross-section which is rectangular, semicircular, elliptical, or substantially circular.

8 Claims, 2 Drawing Sheets

HAIR CIRCLE FOR CONJUGAL AFFECTION

BACKGROUND OF THE INVENTION

This invention is related to the promotion of conjugal affection and especially to a device enabling couples which lack harmony in their sexual lives to have satisfactory passionate affection with each other.

In wedlock, couples usually fail to have sexual satisfaction because of inharmonic responses. Consequently their relationship may become gradually alienated and they even may fear for their sexual life. For erotic satisfaction they often may masturbate for self comfort. According to the an investigative report in "Redbook" three fourths of the 100,000 women interviewed admitted that they had experienced comfort in masturbation. Based upon this it can be concluded that women today are attempting to enjoy such self comfort games. According to a pyschologist's study such behavior is due to a kind of compensation for a deficiency in sexual life. For instance, there is often a difference in the degree of sexual desire between husband and wife. When the side of the stronger desire cannot be satisfied with the opportunity willingly furnished by the other, he or she has no recourse but to take comfort in masturbation for satisfaction.

In view of the above, the instant invention is intended to provide for conjugal affection with an aid to overcoming cases of sexual malfunction, frigidity, or insufficient orgasm (anorgasmia).

SUMMARY OF THE INVENTION

The device of this invention is a hair circle for conjugal affection. The circle has a base member which is flexible and on which several small holes are provided. Soft hairs are positioned to extend through the holes radially outwardly from the upper surface thereof. The hairs may be arranged in rows, transversely, longitudinally, or triangularly. The cross-section of the base member may be a square, semicircular, elliptical or substantially circular. The hairs are caused to adhere to the inner wall of the base member by a plastic film.

DETAILED DESCRIPTION OF THE PREFERRED EMBODIMENT

Figure 1:
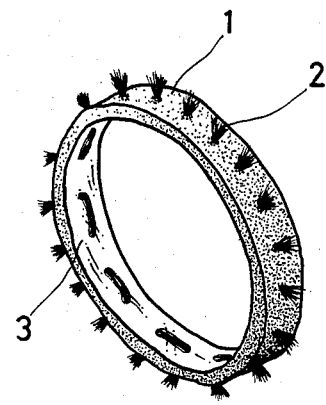
FIG. 1 is a perspective view of an embodiment of this invention.
Figure 2:
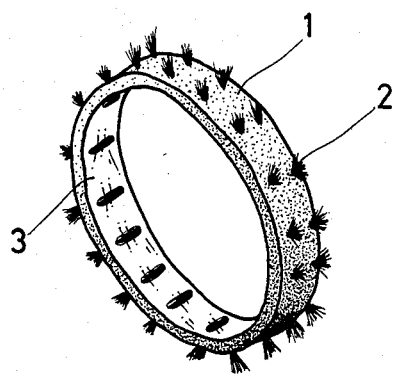
FIG. 2 is a perspective view of an alternative embodiment of this invention.
Figure 3:
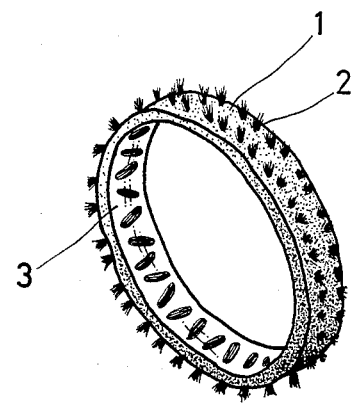
FIG. 3 is a perspective view of an alternative embodiment of this invention.
Figure 4:
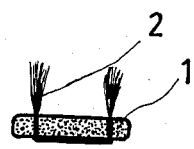
FIG. 4 is a cross-sectional view of another embodiment of this invention.
Figure 5:
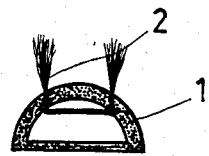
FIG. 5 is a cross-sectional view of another embodiment of this invention.
Figure 7:
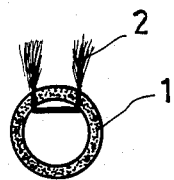
FIG. 7 is a cross-section view of still another embodiment of this invention.
Figure 6:
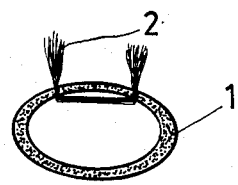
FIG. 6 is a cross-section view of yet another embodiment of this invention.

As shown in FIG. 1, the hair circle for conjugal affection of this invention includes a circular base member 1 on which several small holes are provided for penetration by soft hair tufts extending therethrough. The soft hairs adhere to the base member 1 by means of film 3 which coats the inner surface of the base member 1 covering portions of the tufts. As shown in FIGS. 1–3, the arrangement of soft hair tufts 2 maybe in three types: longitudinal as shown in FIG. 1, transverse as shown in FIG. 2, and triangular as shown in FIG. 3. The cross-section of the base member 1 can be rectangular as shown in FIG. 4, semi-circular as shown in FIG. 5, elliptical as shown in FIG. 6, or substantially circular as shown in FIG. 7.

The hair circle for conjugal affection of this invention is intended to be an aid in cases of sexual inharmony, sexual malfunction, sexual frigidity or insufficient orgasm so as to promote the male's confidence and the female's satisfaction with orgasm in coition.

The distinctive features of this invention are as follows.

1. The hair circle for conjugal affection of this invention is made of an elastic material with attached soft hair tufts to aid in promoting the male's penis expandingly hardened for erection due to phallus congestion and to stimulate the sensitivity of the female's vagina towards complete satisfaction with orgasmic affect.

2. The soft hairs of the hair circle for conjugal affection of this invention can be arranged in rows transversely, longitudinally and triangularly, and the lower part of the elastic base member is equipped with a thin layer for securing the hairs.

3. The cross-section of the elastic base member of the hair circle of this invention can be rectangular, semi-circular, elliptical, or substantially circular as one of its distinctive features.

4. In use, the hair circle of this invention is inserted between the male's glans penis and prepuce (foreskin). As the prepuce is kept behind the glans the hair circle makes the phallus generate wrinkles which provide frictional assistance to the female.

5. The hair circle of this invention contributes to female enjoyment and to the male having a hardened erection. Therefore it can make couples satisfy their sexual demand especially in the case of those suffering from frigidity or insufficient orgasm.

The invention may be embodied in other specified forms without departing from the spirit or essential characteristics thereto. The present embodiments are therefore to be considered in all respects as illustrative and not restrictive, the scope of the invention being indicated by the appended claims rather than by the foregoing description, and all changes which may come within the meaning and range of equivalency of the claims are therefore intended to be embraced therein.

I claim:

1. A hair circle for conjugal affection comprising:
    a circular elastic base member having a plurality of mutually spaced round holes extending radially therethrough, the holes being disposed in a predetermined pattern extending around the circumference of said base member;
    a plurality of tufts of soft hair, an end of each tuft extending through one of said holes so that an end of a tuft extends through each hole with a single tuft having ends extending through a pair of holes;
    an adhered film coating the inner surface of base member to secure said tufts.

2. The device of claim 1 wherein pairs of holes are arranged in rows transverse to said base member.

3. The device of claim 1 wherein pairs of holes are arranged longitudinally along said base member.

4. The device of claim 1 wherein pairs of holes are arranged triangularly along said base member.

5. The device of claim 1 wherein the cross-sectional configuration of said base member is rectangular.

6. The device of claim 1 wherein the cross-sectional configuration of said base member is semicircular.

7. The device of claim 1 wherein the cross-section of said base member is elliptical.

8. The device of claim 1 wherein the cross-section of base members is substantially circular.

* * * * *